(12) United States Patent
Martinez Canovas et al.

(10) Patent No.: US 10,449,344 B2
(45) Date of Patent: Oct. 22, 2019

(54) MICRONEEDLES MADE FROM POLYCARBONATE-POLYCARBONATE/POLY SILOXANE COPOLYMER COMPOSITIONS

(71) Applicant: SABIC GLOBAL TECHNOLOGIES B.V., Bergen op Zoom (NL)

(72) Inventors: Maria Dolores Martinez Canovas, Murcia (ES); Mark Adrianus Johannes Van Der Mee, Breda (NL); Robert Dirk Van De Grampel, Tholen (NL); Johannes De Brouwer, Oisterwijk (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/095,873

(22) PCT Filed: Apr. 28, 2017

(86) PCT No.: PCT/IB2017/052484
§ 371 (c)(1),
(2) Date: Oct. 23, 2018

(87) PCT Pub. No.: WO2017/187410
PCT Pub. Date: Nov. 2, 2017

(65) Prior Publication Data
US 2019/0126025 A1 May 2, 2019

(30) Foreign Application Priority Data
Apr. 28, 2016 (EP) .................................. 16382189

(51) Int. Cl.
*A61M 37/00* (2006.01)
*A61B 5/00* (2006.01)
*C08L 69/00* (2006.01)
*C08L 83/10* (2006.01)
*C08G 77/448* (2006.01)

(52) U.S. Cl.
CPC ......... *A61M 37/0015* (2013.01); *A61B 5/685* (2013.01); *C08L 69/00* (2013.01); *C08L 83/10* (2013.01); *C08G 77/448* (2013.01)

(58) Field of Classification Search
CPC .... A61M 37/0015; A61B 5/685; C08L 69/00; C08L 83/10; C08G 77/448
See application file for complete search history.

(56) References Cited

U.S. PATENT DOCUMENTS

| | | |
|---|---|---|
| 5,504,177 A | 4/1996 | King, Jr. et al. |
| 6,066,700 A | 5/2000 | Konig et al. |
| 7,786,246 B2 | 8/2010 | Jansen et al. |
| 2005/0101757 A1 | 5/2005 | Glasgow et al. |
| 2014/0128811 A1 | 5/2014 | Ferguson et al. |
| 2014/0275368 A1 | 9/2014 | He et al. |
| 2015/0240073 A1 | 8/2015 | Zhao et al. |

FOREIGN PATENT DOCUMENTS

| | | |
|---|---|---|
| AU | 2003301669 B2 | 4/2009 |
| EP | 1685195 A1 | 8/2006 |
| EP | 1757634 A1 | 2/2007 |
| EP | 2455426 A1 | 5/2012 |
| WO | WO 2005/082596 A1 | 9/2005 |
| WO | WO 2013/170456 A1 | 11/2013 |

OTHER PUBLICATIONS

Zhou et al.; "Siloxane modification of polycarbonate for superior flow and impact toughness"; Polymer; vol. 51 Issue 9; Apr. 2010; p. 1990-1999.
"Material Selection with an Eye on Micromolding: A Comparison Study of Materials"; http://www.accu-mold.com/pdf/Accumold-Material_Selection_Study.pdf; Accu-Mold LLC; 2010; 23 pages.
Kelly et al.; "High Shear Strain Rate Rheometry of Polymer Melts"; Journal of Applied Polymer Science; vol. 114; 2009; p. 864-873.
Rannar, Lars-Erik; "On Optimization of Injection Molding Cooling"; http://www.diva-portal.org/smash/get/diva2:124277/FULLTEXT01.pdf.; Thesis; Norwegian University of Science and Technology; Apr. 2008; 147 pages.
International Patent Application No. PCT/IB2017/052484; Int;l Written Opinion and the Search Report; dated Jun. 19, 2017; 9 pages.
International Patent Application No. PCT/IB2017/052484; Int;l Preliminary Report on Patentability; dated Nov. 8, 2018; 14 pages.

*Primary Examiner* — Michael C Miggins
(74) *Attorney, Agent, or Firm* — BakerHostetler

(57) ABSTRACT

A microneedle includes a shaft having a proximal end and a distal end and a capillary space within the shaft, the capillary space (i) connecting the proximal and distal ends or (ii) extending from the distal end of the shaft and connecting with one or more external openings positioned between the proximal end and distal end or (iii) performing the functions of both (i) and (ii). The microneedle includes a polymer mixture which includes (a) optionally polycarbonate, (b) a polycarbonate-polysiloxane copolymer and (c) a mold release agent.

20 Claims, No Drawings

MICRONEEDLES MADE FROM POLYCARBONATE-POLYCARBONATE/POLY SILOXANE COPOLYMER COMPOSITIONS

CROSS-REFERENCE TO RELATED APPLICATION

This application is the National Stage of International Application No. PCT/IB2017/052484, filed Apr. 28, 2017, which claims the benefit of European Application No. 16382189.5 filed Apr. 28, 2016, the disclosures of which are incorporated herein by this reference in their entireties.

TECHNICAL FIELD

The application concerns microneedles made from polycarbonate-polycarbonate/polysiloxane compositions having high flow, high strength, and good release, and methods of forming same.

BACKGROUND

Microneedles are attractive for delivery of certain therapeutics. These needles are virtually painless because they do not penetrate deep enough to touch nerves because, unlike traditional syringes and hypodermic needles, microneedles typically only penetrate the outermost layer of the skin. Additionally, shallower penetration reduces the chance of infection and injury. Furthermore, microneedles facilitate delivery of an exact dosage of a therapeutic which allows use lower doses in treatments.

Microneedles often require a manufacturing process that allows mass production at lowest cost, and as a consequence, shortest possible cycle time. In order to have proper transcription of mold texture and shape to the molded part, high flow may be necessary, especially having low viscosity at extremely high shear rates. Furthermore, good release from the production mold is important to reduce cycle time to improve the cost efficiency. Finally, these needles should have good strength to prevent breaking of the microneedle during usage.

Current materials of choice for microneedles are liquid crystalline polymers, polycarbonate, and polyetherimide. These materials all have certain limitations for microneedle applications. Although liquid crystalline polymers have excellent flow, their mechanical properties depend on the flow direction and needle strength may suffer because of this. Polyetherimide is known for its excellent strength, but the flow of this material is far from optimal and very high temperatures are required to be able to mold this polymer into the desired fine features of a microneedle mold. Polycarbonate is flexible in molding conditions, easily formable and has acceptable mechanical properties for the application in microneedles. At high shear rates though, around and beyond $10^6$ inverse seconds ($s^{-1}$), a plateau value in viscosity may be reached. In some cases, a further increase in shear rate even causes shear thickening behavior which makes filling the fine microfeatures in microneedles molds more difficult. The shear thickening phenomenon is thought to be caused by molecular orientation in the melt.

The fine featured microneedles require excellent mold release properties in order not to get damaged. This can be achieved by cooling the mold deeper than for typical molding operations, but requires an increased expense of energy cost and cycle time and is in general an uneconomic solution. Alternatively, there is a variety of commercial mold release additives such as pentaerythritol tetrastearate (PETS) and waxes that improve mold release behavior, but (traces of) such compounds may remain in the mold and build a deposit after a number of molding cycles which may directly impact needle shape and sharpness.

These and other shortcomings are addressed by aspects of the present disclosure.

SUMMARY

Aspects of the disclosure concern microneedles comprising a shaft having a proximal end and a distal end and a capillary space within said shaft, said capillary space (i) connecting said proximal and distal ends or (ii) extending from the distal end of the shaft and connecting with one or more external openings positioned between the proximal end and distal end or (iii) performing the functions of both (i) and (ii); said microneedle comprising a polymer mixture which comprises (a) polycarbonate, (b) polycarbonate-polysiloxane copolymer and (c) mold release agent.

Other aspects concern medical devices suitable for delivery of a therapeutic agent, said device comprising one or more microneedles disclosed herein.

Yet further aspects concern methods of forming a microneedle comprising (a) placing a polymer mixture into a mold, said polymer mixture comprising a polymer mixture which comprises (i) polycarbonate, (ii) polycarbonate-polysiloxane copolymer and (iii) mold release agent; and (b) releasing said polymer mixture from said mold.

DETAILED DESCRIPTION OF ILLUSTRATIVE EMBODIMENTS

The present disclosure can be understood more readily by reference to the following detailed description of the disclosure and the Examples included therein.

Microneedle

Microneedles can be used to deliver a therapeutic or to draw blood without penetrating tissue as deep a traditional needles. Such microneedles can be used individually or as an array of needles. The size of such needles typically is measured in microns. Some microneedles are between 100 micrometers (microns, μm) and 1 millimeter (mm) in length (or about 100 μm to about 1 mm), preferably between 10 μm and 500 μm (or about 10 μm and about 500 μm), more preferably between 30 μm and 200 μm (or about 30 μm and about 200 μm) and more preferably between 100 μm and 150 μm (or about 100 μm and about 150 μm).

Microneedles are hollow—containing at least one substantially annular bore or channel with a diameter large enough to permit passage of a drug-containing fluid the microneedle. The hollow shafts may be linea—extending from needle base to needle tip. Other microneedles can have a more complex path—for example, extending from the needle base, but then lead to one or more openings on the sides of the needle rather than an opening at the needle tip. Shafts may be tapered or uniform in diameter depending on utility needs.

In some aspects, microneedles comprise a shaft having a proximal end and a distal end, a capillary space within said shaft connecting said proximal and distal ends. One utility of microneedles is as part of a medical device that delivers a therapeutic within a patient. Certain medical devices comprise a plurality of microneedles.

Microneedles should have sufficient mechanical strength to remain intact (i) while being inserted into the biological barrier, (ii) while remaining in place for up to a number of days, and (iii) while being removed. Microneedles can be sterilized prior to use.

Microneedles can be manufactured via commercial molding technology. In one aspect, the polymer mixture is supplied in a liquid or flowable state to a mold and allowed to solidify. The solid product is then separated from the mold.

Polycarbonate Polymer

The terms "polycarbonate" or "polycarbonates" as used herein includes copolycarbonates, homopolycarbonates and (co)polyester carbonates.

The term polycarbonate can be further defined as compositions have repeating structural units of the formula (1):

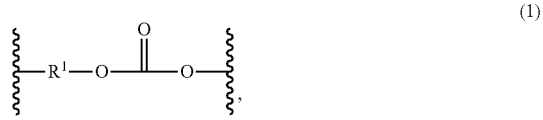

(1)

in which at least 60 percent of the total number of $R^1$ groups are aromatic organic radicals and the balance thereof are aliphatic, alicyclic, or aromatic radicals. In a further aspect, each $R^1$ is an aromatic organic radical and, more preferably, a radical of the formula (2):

$$-A^1-Y^1-A^2-$$ (2), wherein each of $A^1$ and $A^2$ is a monocyclic divalent aryl radical and $Y^1$ is a bridging radical having one or two atoms that separate $A^1$ from $A^2$. In various aspects, one atom separates $A^1$ from $A^2$. For example, radicals of this type include, but are not limited to, radicals such as —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ is preferably a hydrocarbon group or a saturated hydrocarbon group such as methylene, cyclohexylidene, or isopropylidene. Polycarbonate materials include materials disclosed and described in U.S. Pat. No. 7,786,246, which is hereby incorporated by reference in its entirety for the specific purpose of disclosing various polycarbonate compositions and methods for manufacture of same. Polycarbonate polymers can be manufactured by means known to those skilled in the art.

Apart from the main polymerization reaction in polycarbonate production, there is a series of side reactions consisting of chain rearrangements of the polymer backbone that lead to branching that are often referred to as Fries rearrangement. The Fries species specifically found in bisphenol A melt polycarbonates are the ester type of structures A, B, and C.

A. Linear Fries:

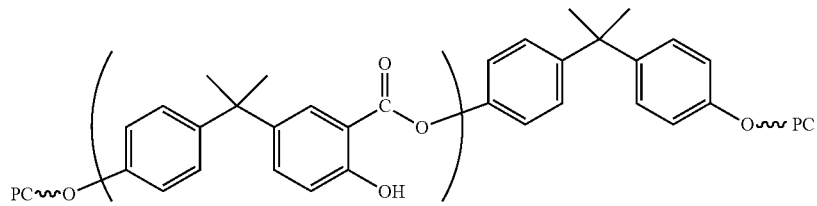

B. Branched Fries:

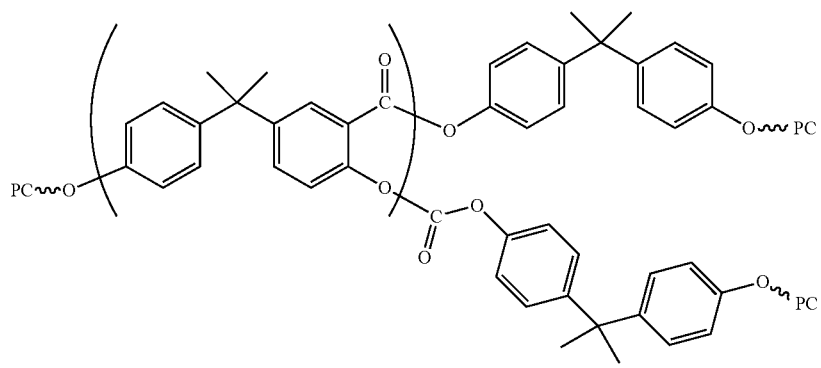

C. Acid Fries:

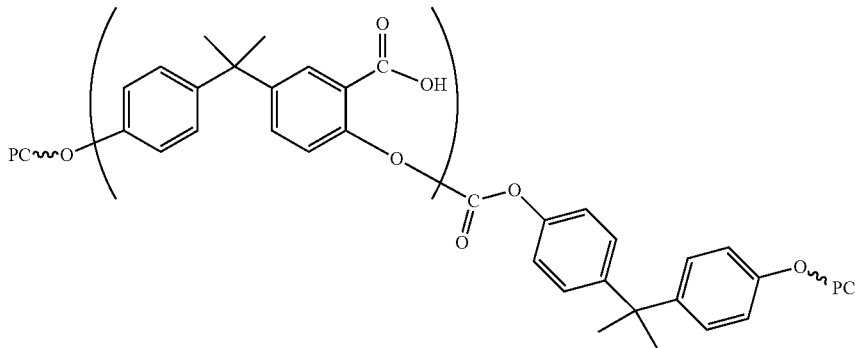

The Fries reaction is induced by the combined effect of basic catalysts, temperature, and residence time, which makes the melt-produced polycarbonates inherently branched as compared with the interfacial polycarbonates since their manufacturing temperatures are lower. Because high branching levels in the resin can have a negative effect on the mechanical properties of the polycarbonate (for example, on impact strength), a product with lower branched Fries product is preferred.

In certain aspects, polycarbonate produced by interfacial polymerization may be utilized. In some processes, bisphenol A and phosgene are reacted in an interfacial polymerization process. Typically, the disodium salt of bisphenol A is dissolved in water and reacted with phosgene which is typically dissolved in a solvent that not miscible with water (such as a chlorinated organic solvent like methylene chloride).

In some aspects, the polycarbonate comprises interfacial polycarbonate having a weight average molecular weight of from about 10,000 Daltons to about 50,000 Daltons, preferably about 15,000 to about 45,000 Daltons. Some interfacial polycarbonates have and endcap level of at least 90% or preferably 95%.

A melt polycarbonate product may also be utilized. The melt polycarbonate process is based on continuous reaction of a dihydroxy compound and a carbonate source in a molten stage. The reaction can occur in a series of reactors where the combined effect of catalyst, temperature, vacuum, and agitation allows for monomer reaction and removal of reaction by-products to displace the reaction equilibrium and effect polymer chain growth. A common polycarbonate made in melt polymerization reactions is derived from bisphenol A (BPA) via reaction with diphenyl carbonate (DPC). This reaction can be catalyzed by, for example, tetra methyl ammonium hydroxide (TMAOH) or tetrabutyl phosphonium acetate (TBPA), which can be added in to a monomer mixture prior to being introduced to a first polymerization unit and sodium hydroxide (NaOH), which can be added to the first reactor or upstream of the first reactor and after a monomer mixer.

The melt polycarbonate may have a molecular weight (Mw) of 20,000 to 120,000 Dalton on a polystyrene basis The melt polycarbonate product may have an endcap level of 45% to 80%, or about 45% to about 80%. Some polycarbonates have an endcap level of 45% to 75% or about 45% to about 75%, 55% to 75% or about 55% to about 75%, 60% to 70 or about 60% to about 70%, 60% to 65% or about 60% to about 65%. Certain preferred polycarbonates have at least 200 parts per million (ppm) of hydroxide groups.

Certain polycarbonates have 200 ppm to 1100 ppm (or about 200 ppm to about 1100 ppm) or 950 ppm to 1050 ppm (or about 950 ppm to 1050 ppm) hydroxide groups.

Polycarbonate polymer may contain endcapping agents. Any suitable endcapping agents can be used provided that such agents do not significantly adversely impact the desired properties of the polycarbonate composition (transparency, for example). Endcapping agents include mono-phenolic compounds, mono-carboxylic acid chlorides, and/or mono-chloroformates. Mono-phenolic endcapping agents are exemplified by monocyclic phenols such as phenol and $C_1$-$C_{22}$ alkyl-substituted phenols such as p-cumyl-phenol, resorcinol monobenzoate, and p- and tertiary-butyl phenol; and monoethers of diphenols, such as p-methoxyphenol.

Additionally, some polycarbonates have 900 ppm to 1100 ppm (or about 900 ppm to about 1100 ppm) and 950 ppm to 1050 ppm (or about 950 ppm to about 1050 ppm) of Fries products. Fries products include ester type of structures A, B, and C.

Polycarbonate-Polysiloxane Copolymer

As used herein, the term "polycarbonate-polysiloxane copolymer" is equivalent to polysiloxane-polycarbonate copolymer, polycarbonate-polysiloxane polymer, or polysiloxane-polycarbonate polymer. In various aspects, the polycarbonate-polysiloxane copolymer can be a block copolymer comprising one or more polycarbonate blocks and one or more polysiloxane blocks. In some aspects, the polysiloxane-polycarbonate copolymer comprises polydiorganosiloxane blocks comprising structural units of the general formula (13) below:

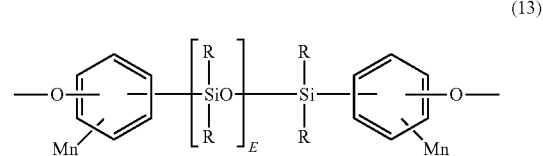

(13)

wherein the polydiorganosiloxane block length (E) is from about 20 to about 60; wherein each R group can be the same or different, and is selected from a $C_{1-13}$ monovalent organic group; wherein each M can be the same or different, and is selected from a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ aralkyl, $C_7$-$C_{12}$ aralkoxy, $C_7$-$C_{12}$ alkylaryl, or $C_7$-$C_{12}$ alkylaryloxy, and where each n is independently 0, 1, 2, 3, or 4. The polysiloxane-polycarbonate copolymer also comprises polycarbonate blocks comprising structural units of the general formula (14) below:

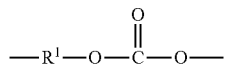
(14)

wherein at least 60 percent of the total number of $R^1$ groups comprise aromatic moieties and the balance thereof comprise aliphatic, alicyclic, or aromatic moieties.

Certain polycarbonate-polysiloxane resins comprise allylphenol capped siloxanes. Such resins comprise the structure:

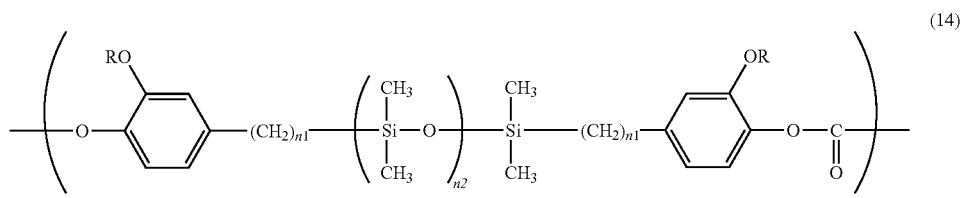
(14)

where R is an alkyl group having 1-3 carbon atoms, n1 is an integer of from 2 to 4, and n2 is an integer of from 1 to 200. Polycarbonate-polysiloxane copolymers comprising such structures can be found in European Patent Application No. 1757634 which is hereby incorporated by reference in its entirety for the specific purpose of disclosing various compositions and methods for manufacture of same.

Certain polysiloxane-polycarbonates materials include materials disclosed and described in U.S. Pat. No. 7,786,246, which is hereby incorporated by reference in its entirety for the specific purpose of disclosing various compositions and methods for manufacture of same.

The polycarbonate-siloxane copolymer comprises 4 weight percent (wt. %) to 97 wt % siloxane, or from about 4 wt. % to about 97 wt. % siloxane. In some preferred aspects, the polycarbonate-siloxane copolymer comprises 4 wt. % to 30 wt. % siloxane, or from about 4 wt. % to about 30 wt. % siloxane. In some copolymers, the amount of siloxane is 4 wt. % to 15 wt. % or from about 4 wt. % to about 15 wt %, or 3.5 wt. % to 22 wt. % or from about 3.5 to about 22 wt. % siloxane, or from 4 wt. % to 25 wt. % or from about 4 wt. % to about 25 wt. %. One preferred aspect comprises 20 wt. % or about 20 wt. % siloxane.

Non-limiting examples of polysiloxane-polycarbonate copolymers can comprise various copolymers available from SABIC Innovative plastics. In an aspect, the polysiloxane-polycarbonate copolymer can contain 6% by weight polysiloxane content based upon the total weight of the polysiloxane-polycarbonate copolymer. In various aspects, the 6% by weight polysiloxane block copolymer can have a weight average molecular weight (Mw) of from about 23,000 to 24,000 Daltons using gel permeation chromatography with a bisphenol A polycarbonate absolute molecular weight standard. In certain aspects, the 6% weight siloxane polysiloxane-polycarbonate copolymer can have a melt volume flow rate (MVR) of about 10 cm3/10 min at 300° C./1.2 kg (see C9030T, a 6% by weight polysiloxane content copolymer available from SABIC Innovative Plastics as "transparent" EXL C9030T resin polymer). In another example, the polysiloxane-polycarbonate block can comprise 20% by weight polysiloxane based upon the total weight of the polysiloxane block copolymer. For example, an appropriate polysiloxane-polycarbonate copolymer can be a bisphenol A polysiloxane-polycarbonate copolymer endcapped with para-cumyl phenol (PCP) and having a 20% polysiloxane content (see C9030P, commercially available from SABIC Innovative Plastics as the "opaque" EXL C9030P). In various aspects, the weight average molecular weight of the 20% polysiloxane block copolymer can be about 29,900 Daltons to about 31,000 Daltons when tested according to a polycarbonate standard using gel permeation chromatography (GPC) on a cross-linked styrene-divinylbenzene column and calibrated to polycarbonate references using a UV-VIS detector set at 264 nm on 1 mg/ml samples eluted at a flow rate of about 1.0 ml/minute. Moreover, the 20% polysiloxane block copolymer can have an MVR at 300° C./1.2 kg of 7 cm3/10 min and can exhibit siloxane domains sized in a range of from about 5 micron to about 20 micrometers (microns, μm).

Release Agent

Examples of mold release agents include both aliphatic and aromatic carboxylic acids and their alkyl esters, for example, stearic acid, behenic acid, pentaerythritol tetrastearate, glycerin tristearate, and ethylene glycol distearate. Polyolefins such as high-density polyethylene, linear low-density polyethylene, low-density polyethylene, and similar polyolefin homopolymers and copolymers can also be used a mold release agents.

Some compositions use pentaerythritol tetrastearate, glycerol monosterate, a wax or a poly alpha olefin.

Mold release agents are typically present in the composition at 0.05 wt. % to 10 wt. % or about 0.05 wt. % to about 10 wt. %, based on total weight of the composition, specifically 0.1 wt. % to 5 wt % or about 0.1 wt. % to about 5 wt. %, 0.1 wt. % to 1 wt. % or about 0.1 wt. % to about 1 wt. %, or 0.1 wt. % to 0.5 wt. % or about 0.1 wt. % to about 0.5 wt. %. Some preferred mold release agents will have high molecular weight, typically greater than 300, to prevent loss of the release agent from the molten polymer mixture during melt processing.

Additional Components

The additive composition can include an impact modifier, flow modifier, antioxidant, heat stabilizer, light stabilizer, ultraviolet (UV) light stabilizer, UV absorbing additive, plasticizer, lubricant, antistatic agent, anti-fog agent, antimicrobial agent, colorant (e.g., a dye or pigment), surface effect additive, radiation stabilizer, anti-drip agent (e.g., a PTFE-encapsulated styrene-acrylonitrile copolymer (TSAN)), or a combination comprising one or more of the foregoing. For example, a combination of a heat stabilizer, and ultraviolet light stabilizer can be used. In general, the additives are used in the amounts generally known to be effective. For example, the total amount of the additive composition can be 0.001 to 10.0 wt %, or 0.01 to 5 wt %, each based on the total weight of all ingredients in the composition.

The composition can include various additives ordinarily incorporated into polymer compositions of this type, with the proviso that the additive(s) are selected so as to not significantly adversely affect the desired properties of the thermoplastic composition (good compatibility for example). Such additives can be mixed at a suitable time during the mixing of the components for forming the composition.

Examples of impact modifiers include natural rubber, fluoroelastomers, ethylene-propylene rubber (EPR), ethylene-butene rubber, ethylene-propylene-diene monomer rubber (EPDM), acrylate rubbers, hydrogenated nitrile rubber (HNBR), silicone elastomers, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MBS), high rubber graft (HRG), and the like. Some suitable impact modifies include PC(polycarbonate)/ABS (such as Cycoloy PC/ABS) and MBS type formulations.

Heat stabilizer additives include organophosphites (e.g. triphenyl phosphite, tris-(2,6-dimethylphenyl)phosphite, tris-(mixed mono- and di-nonylphenyl)phosphite or the like), phosphonates (e.g., dimethylbenzene phosphonate or the like), phosphates (e.g., trimethyl phosphate, or the like), or combinations comprising at least one of the foregoing heat stabilizers. The heat stabilizer can be tris(2,4-di-t-butylphenyl) phosphate available as Irgafos™ 168. Heat stabilizers are generally used in amounts of 0.01 to 5 wt %, or about 0.01 wt. % to about 5 wt. %, based on the total weight of polymer in the composition.

There is considerable overlap among plasticizers, lubricants, and mold release agents, which include, for example, glycerol tristearate (GTS), phthalic acid esters (e.g., octyl-4,5-epoxy-hexahydrophthalate), tris-(octoxycarbonylethyl) isocyanurate, tristearin, di- or polyfunctional aromatic phosphates (e.g., resorcinol tetraphenyl diphosphate (RDP), the bis(diphenyl) phosphate of hydroquinone and the bis(diphenyl) phosphate of bisphenol A); poly-alpha-olefins; epoxidized soybean oil; silicones, including silicone oils (e.g., poly(dimethyl diphenyl siloxanes); esters, for example, fatty acid esters (e.g., alkyl stearyl esters, such as, methyl stearate, stearyl stearate, and the like), polyethylene, waxes (e.g., beeswax, montan wax, paraffin wax, or the like), or combinations comprising at least one of the foregoing plasticizers, lubricants, and mold release agents. These are generally used in amounts of 0.01 to 5 wt %, or about 0.01 wt. % to about 5 wt. %, based on the total weight of the polymer in the composition.

Light stabilizers, in particular ultraviolet light (UV) absorbing additives, also referred to as UV stabilizers, include hydroxybenzophenones (e.g., 2-hydroxy-4-n-octoxy benzophenone), hydroxybenzotriazines, cyanoacrylates, oxanilides, benzoxazinones (e.g., 2,2'-(1,4-phenylene)bis (4H-3,1-benzoxazin-4-one, commercially available under the trade name CYASORB UV-3638 from Cytec), aryl salicylates, hydroxybenzotriazoles (e.g., 2-(2-hydroxy-5-methylphenyl)benzotriazole, 2-(2-hydroxy-5-tert-octylphenyl)benzotriazole, and 2-(2H-benzotriazol-2-yl)-4-(1,1,3,3-tetramethylbutyl)-phenol, commercially available under the trade name CYASORB 5411 from Cytec) or combinations comprising at least one of the foregoing light stabilizers. The UV stabilizers can be present in an amount of 0.01 wt. % to 1 wt. % or about or about 0.01 wt. % to about 1 wt. %, specifically, 0.1 wt. % to 0.5 wt. % or about 0.01 wt. % to about 0.5 wt. %, and more specifically, 0.15 wt. % to 0.4 wt. % or about 0.01 wt. % to about 0.4 wt. %, based upon the total weight of polymer in the composition.

Antioxidant additives include organophosphites such as tris(nonyl phenyl)phosphite, tris(2,4-di-t-butylphenyl)phosphite, bis(2,4-di-t-butylphenyl)pentaerythritol diphosphite, distearyl pentaerythritol diphosphite; alkylated monophenols or polyphenols; alkylated reaction products of polyphenols with dienes, such as tetrakis[methylene(3,5-di-tert-butyl-4-hydroxyhydrocinnamate)] methane; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl) propionate; amides of beta-(3,5-di-tert-butyl-4-hydroxyphenyl)-propionic acid, or combinations comprising at least one of the foregoing antioxidants. Antioxidants are used in amounts of 0.01 to 0.1 parts by weight (pbw), or about 0.1 pbw to about 0.1 pbw, based on 100 parts by weight of the total composition, excluding any filler.

Anti-drip agents can also be used in the composition, for example a fibril forming or non-fibril forming fluoropolymer such as polytetrafluoroethylene (PTFE). The anti-drip agent can be encapsulated by a rigid copolymer, for example styrene-acrylonitrile copolymer (SAN). PTFE encapsulated in SAN is known as TSAN. A TSAN comprises 50 wt. % PTFE and 50 wt. % SAN, based on the total weight of the encapsulated fluoropolymer. The SAN can comprise, for example, 75 wt. % styrene and 25 wt. % acrylonitrile based on the total weight of the copolymer. Antidrip agents can be used in amounts of 0.1 pbw to 10 pbw or about 0.1 pbw to about 10 pbw, based on 100 parts by weight of the total composition, excluding any filler.

Polymer Mixtures

Some polymer mixtures comprise (a) optionally polycarbonate, (b) polycarbonate-polysiloxane copolymer and (c) mold release agent. Certain polymer mixtures used in the disclosure comprise:

from 30 wt. % to 89.5 wt. % or from about 30 to about 89.5 wt. % polycarbonate (PC);

from 10 wt. % to 69.5 wt. % or from about 10 to about 69.5 wt. % polycarbonate-polysiloxane copolymer; and from 0.1 wt. % to 0.5 wt. % or from about 0.1 to about 0.5 wt. % mold release agent; wherein all wt. % values are based on the total weight of the polymer mixture.

Other mixtures comprise from 70 wt. % to 89.5 wt. % or from about 70 to about 89.5 wt. % polycarbonate and from 10 wt. % to 30 wt. % or from about 10 to about 30 wt. % polycarbonate-siloxane copolymer.

The polymer mixture preferably has a melt volume flow rate (MVR) of greater than 30 cubic centimeters per minute ($cm^3$/min), 35 $cm^3$/min, 40 $cm^3$/min, or more preferably 50 $cm^3$/min as measured according to ASTM 1133 at 300 degrees Celsius (° C.) and 1.2 kilograms (kg).

The polymer mixture preferably has an Izod Notched Impact of at least 35 kilojoules per square meter ($kJ/m^2$) or 40 $kJ/m^2$ or more preferably at least 50 $kJ/m^2$ as measured according to ISO 180-1A.

The polymer mixture preferably has a heat deflection temperature (HDT) of at least 120° C. on a 3.2 millimeter (mm) sample at 1.8 megapasacals MPa as measured according to ASTM D648.

In addition, the polymer mixture preferably exhibits excellent release, as measured by ejection force (N) and coefficient of friction. Release performance is significantly better for the compositions of the disclosure compared with than for commercial alternatives, including high flow PC, impact modified PC and standard flow Lexan™ EXL.

The polymer mixtures also preferably show (i) high flow at high shear conditions to allow good transcription of mold texture and excellent filling of the finest mold features, (ii) good strength and impact (as indicated by ductile Izod Notched Impact at room temperature and modulus), and (iii) high release to have efficient de-molding and reduced cooling and cycle time during molding.

Definitions

It is to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural equivalents unless the context clearly dictates otherwise. Thus, for example, reference to "a polycarbonate polymer" includes mixtures of two or more polycarbonate polymers.

Ranges can be expressed herein as from one particular value to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±5% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

"ppm" refers to parts per million.

As used herein the terms "weight percent," "weight %," and "wt. %" of a component, which can be used interchangeably, unless specifically stated to the contrary, are based on the total weight of the formulation or composition in which the component is included. For example if a particular element or component in a composition or article is said to have 8% by weight, it is understood that this percentage is relative to a total compositional percentage of 100% by weight.

As used herein, the terms "weight average molecular weight" or "Mw" can be used interchangeably, and are defined by the formula:

$$M_w = \frac{\sum N_i M_i^2}{\sum N_i M_i},$$

where Mi is the molecular weight of a chain and Ni is the number of chains of that molecular weight. Mw can be determined for polymers, e.g. polycarbonate polymers, by methods well known to a person having ordinary skill in the art using molecular weight standards, e.g. polycarbonate standards or polystyrene standards, preferably certified or traceable molecular weight standards. Polystyrene basis refers to measurements using a polystyrene standard.

The term "siloxane" refers to a segment having a Si—O—Si linkage.

The term "flowable" means capable of flowing or being flowed. Typically a polymer is heated such that it is in a melted state to become flowable.

° C. is degrees Celsius. µm is micrometer. cS is centistroke. kG is kilogram.

"Interfacial polycarbonate" is produced by a process where typically the disodium salt of bisphenol A (BPA) is dissolved in water and reacted with phosgene which is typically dissolved in a solvent that not miscible with water.

"Melt polycarbonate" is produced by a process where BPA reacts with diphenyl carbonate (DPC) in a molten state without the solvent.

Izod Notched Impact tests are performed according to ISO 180-1A.

Melt Volume Flow Rate (MVR) is measured according to ASTM 1133 at 300° C. and 1.2 kg.

Heat deflection temperature (HDT) is measured using a 3.2 mm sample at 1.8 MPa as measured according to ISO 75A.

Unless specified to the contrary herein, all test standards are the most recent standard in effect at the time of filing this application.

Aspects

The present disclosure comprises at least the following aspects.

Aspect 1. A microneedle comprising a shaft having a proximal end and a distal end and a capillary space within said shaft, said capillary space (i) connecting said proximal and distal ends or (ii) extending from the distal end of the shaft and connecting with one or more external openings positioned between the proximal end and distal end or (iii) performing the functions of both (i) and (ii), said microneedle comprising a polymer mixture which comprises (a) optionally polycarbonate, (b) polycarbonate-polysiloxane copolymer, and (c) mold release agent.

Aspect 2. A microneedle consisting essentially of: a shaft having a proximal end and a distal end and a capillary space within said shaft, said capillary space (i) connecting said proximal and distal ends or (ii) extending from the distal end of the shaft and connecting with one or more external openings positioned between the proximal end and distal end or (iii) performing the functions of both (i) and (ii), said microneedle comprising a polymer mixture which comprises (a) optionally polycarbonate, (b) polycarbonate-polysiloxane copolymer, and (c) mold release agent.

Aspect 3. A microneedle consisting of: a shaft having a proximal end and a distal end and a capillary space within said shaft, said capillary space (i) connecting said proximal and distal ends or (ii) extending from the distal end of the shaft and connecting with one or more external openings positioned between the proximal end and distal end or (iii) performing the functions of both (i) and (ii), said microneedle comprising a polymer mixture or composition which comprises (a) optionally polycarbonate, (b) polycarbonate-polysiloxane copolymer, and (c) mold release agent.

Aspect 4. The microneedle of any of aspects 1-3 formed from a polymer mixture comprising: about 0 wt. % to about 94.9 wt. % polycarbonate; about 5 to about 99.9 wt. % polycarbonate-polysiloxane copolymer; and about 0.1 to about 1 wt. % mold release agent; wherein the combined weight percent value of all components does not exceed about 100 wt. %, and wherein all weight percent values are based on the total weight of the polymer mixture.

Aspect 5. The microneedle of any of aspects 1-3 formed from a polymer mixture comprising: about 0 wt. % to 94.9 wt. % polycarbonate; 5 wt. % to 99.9 wt. % polycarbonate-polysiloxane copolymer; and 0.1 wt. % to 1 wt. % mold release agent; wherein the combined weight percent value of all components does not exceed about 100 wt. %, and wherein all weight percent values are based on the total weight of the composition.

Aspect 6. The microneedle of any of aspects 1-5, wherein said polymer mixture has a melt volume flow rate (MVR) of greater than 35 $cm^3$/min as measured according to ASTM 1133 at 300° C. and 1.2 kg.

Aspect 7. The microneedle of any of aspects 1-5, wherein said polymer mixture has a Izod Notched Impact strength of at least 35 $kJ/m^2$ as measured at 3 mm thickness according to ISO 180-1A.

Aspect 8. The microneedle of any of aspects 1-7, wherein the polycarbonate-siloxane copolymer comprises 4 wt. % to 97 wt. % siloxane based on the weight of the copolymer.

Aspect 9. The microneedle of any of aspects 1-7, wherein the polycarbonate-siloxane copolymer comprises about 4 wt. % to about 97 wt. % siloxane based on the weight of the copolymer.

Aspect 10. The microneedle of any of aspects 1-9, wherein said polymer mixture comprises 70 wt. % to 89.5 wt. % polycarbonate and 10 wt. % to 30 wt. % polycarbonate-siloxane copolymer.

Aspect 11. The microneedle of any of aspects 1-9, wherein said polymer mixture comprises about 70 wt. % to about 89.5 wt. % polycarbonate and about 10 wt. % to about 30 wt. % polycarbonate-siloxane copolymer.

Aspect 12. The microneedle of any of aspects 1-11, wherein said polycarbonate comprises interfacial polycarbonate.

Aspect 13. The microneedle of any of aspects 1-11, wherein said polycarbonate comprises melt polycarbonate.

Aspect 14. The microneedle of any of aspects 1-13, wherein said mold release agent comprises one or more of pentaerythritol stearate, glycerol monostearate, a wax, polyethylene or a poly alpha olefin.

Aspect 15. The microneedle of any of aspects 1-14, wherein said microneedle consists of said polymer mixture.

Aspect 16. The microneedle of any of aspects 1-15, wherein said polymer mixture has a heat deflection temperature (HDT) of at least 120° C. on a 3.2 mm sample at 1.8 MPa as measured according to ISO 75A.

Aspect 17. A medical device suitable for delivery of a therapeutic agent, said device comprising one or more microneedles of any one of clams 1-16.

Aspect 18. A method of forming a microneedle comprising: (a) placing a polymer mixture into a mold, said polymer mixture comprising (i) optionally polycarbonate, (ii) polycarbonate-polysiloxane copolymer and (iii) mold release agent, said polymer mixture being at a temperature such that it is flowable; (b) allowing said polymer to solidify; and (c) releasing said solidified polymer mixture from said mold.

Aspect 19. The method of aspect 18, wherein said polymer mixture comprises: about 0 wt. % to 94.9 wt. % polycarbonate; 5 wt. % to 99.9 wt. % polycarbonate-polysiloxane copolymer; and 0.1 wt. % to 1 wt. % mold release agent; wherein the combined weight percent value of all components does not exceed about 100 wt. %, and wherein all weight percent values are based on the total weight of the polymer mixture.

Aspect 20. The method of aspect 18, wherein said polymer mixture comprises: about 0 wt. % to about 94.9 wt. % polycarbonate; about 5 wt. % to about 99.9 wt. % polycarbonate-polysiloxane copolymer; and about 0.1 wt. % to about 1 wt. % mold release agent; wherein the combined weight percent value of all components does not exceed about 100 wt. %, and wherein all weight percent values are based on the total weight of the polymer mixture.

Aspect 21. The method of any of aspects 18-20, wherein said polymer mixture has a melt volume flow rate (MVR) of greater than 35 cm$^3$/min as measured according to ASTM 1133 at 300° C. and 1.2 kg.

Aspect 22. The method of any of aspects 18-21, wherein the polycarbonate-siloxane copolymer comprises 4 wt. % to 97 wt. % siloxane.

Aspect 23. The method of any of aspects 18-21, wherein the polycarbonate-siloxane copolymer comprises about 4 to about 97 wt. % siloxane.

Aspect 24. The method of any of aspects 18-23, wherein said polycarbonate comprises interfacial polycarbonate.

Aspect 25. The method of any of aspects 18-23, wherein said polycarbonate comprises melt polycarbonate.

Aspect 26. The method of any of aspects 18-25, wherein said mold release agent comprises one or more of pentaerythritol stearate, glycerol monostearate, polyethylene, a wax or a poly alpha olefin.

Aspect 27. The method of any of aspects 18-26, wherein said polymer mixture comprises 70 wt. % to 89.5 wt. % polycarbonate and about 10 wt. % to about 30 wt. % polycarbonate-siloxane copolymer.

Aspect 28. The method of any of aspects 18-26, wherein said polymer mixture comprises about 70 to about 89.5 wt. % polycarbonate and about 10 to about 30 wt. % polycarbonate-siloxane copolymer.

Examples

The disclosure is illustrated by the following non-limiting examples. A number of polymer blends were prepared from the components described below. The components of Tables 1 and 2 are used to form polymer blends and molded into microneedles using conventional technology. Such microneedles can be integrated into medical devices used for drawing blood from a patient or delivery of therapeutic agents to a patient.

PC-PS1 is a transparent BPA polycarbonate-polydimethylsiloxane block copolymer comprising about 6 wt. % siloxane (PDMS residues). PC-PS1 has an Mw of 22,500-23,500 g/mol in PC equivalent units (measured on a size exclusion column calibrated with broad molar mass polycarbonate standards of known mass determined through light scattering). PC PS1 is made through an interfacial polymerization process using para-cumyl phenol as end-cap.

PC-PS2 is an opaque BPA polycarbonate-polydimethylsiloxane block copolymer comprising about 20 wt. % of siloxane (PDMS residues). PC-PS2 has an Mw of 30,000-31,000 g/mol in PC equivalent units (measured on a size exclusion column calibrated with broad molar mass polycarbonate standards of known mass determined through light scattering). PC-PS2 is made through an interfacial polymerization process using para-cumyl phenol as end-cap. The material is sold by SABIC™ Innovative Plastics under the tradename LEXAN™.

PCI is an optical quality BPA polycarbonate. PCI has an Mw of 18,400-19,000 g/mol in PC equivalent units (measured on a size exclusion column calibrated with broad molar mass polycarbonate standards of known mass determined through light scattering). PC1 is made through an interfacial polymerization process using para-cumyl phenol as end-cap. MVR measured at 300° C. and 1.2 kg is 60 to 85.

PC2 is an optical quality BPA polycarbonate. PC2 has an Mw 18,500-19,000 g/mol in PC equivalent units (measured on a size exclusion column calibrated with broad molar mass polycarbonate standards of known mass determined through light scattering). PC2 is made using a melt bulk polymerization process. MVR measured at 300° C. and 1.2 kg is 60 to 85, with a phenol end-cap level more the 85% and a fries level lower than 400 ppm.

A number of additives are included among the formulations. The poly alpha olefin used has a viscosity of 6 centistrokes (cS) at 100° C. Tospearl™ 120 is a microfine silicone resin marketed by Momentive. PETS is pentaerythritol tetrastearate, greater than 90% esterified, and is used as a mold release agent, tradename PETS G by Faci. The phosphite stabilizer tris(2,4-di-tert-butylpheyl) phosphite having the tradename Irgafos™ 168 and marketed by Ciba was used in the examples. Phosphorous acid $H_3PO_3$ (45%) was also used as a phosphite stabilizer. Talc was used as mineral filler. Fumed silica surfaced treated with polydimethyl siloxane (PDMS), available as was included in the examples.

Examples 1-9 and Examples 10-18 are prepared and evaluated according to the values presented in Tables 2 and 3, respectively. The compositions vary the amount and molecular weight of the polycarbonate and polycarbonate-polydimethylsiloxane block copolymers as well as the remaining components and additives. All values are in weight percent (wt. %) based on the total weight of the particular example.

TABLE 1

Formulations and properties for Examples 1-9.

| Description | Ex 1 | Ex 2 | Ex 3 | Ex 4 | Ex 5 | Ex 6 | Ex 7 | Ex 8 | Ex 9 |
|---|---|---|---|---|---|---|---|---|---|
| PC-PS1 | 37.5 | 0 | 37.5 | 0 | 50 | 0 | 66.7 | 0 | 0 |
| PC-PS2 | 0 | 11.25 | 0 | 11.25 | 0 | 15 | 0 | 20 | 11.25 |
| PC1 | 62.09 | 88.34 | 0 | 0 | 49.59 | 84.59 | 32.89 | 79.59 | 88.29 |
| PC2 | 0 | 0 | 62.09 | 88.34 | 0 | 0 | 0 | 0 | 0 |
| Tris(di-butylphenyl) phosphite | 0.06 | 0.06 | 0.06 | 0.06 | 0.06 | 0.06 | 0.06 | 0.06 | 0.06 |
| Poly alpha olefin, 6 cS/100° C. | 0.35 | 0.35 | 0.35 | 0.35 | 0.35 | 0.35 | 0.35 | 0.35 | 0.35 |

TABLE 1-continued

Formulations and properties for Examples 1-9.

| Description | Ex 1 | Ex 2 | Ex 3 | Ex 4 | Ex 5 | Ex 6 | Ex 7 | Ex 8 | Ex 9 |
|---|---|---|---|---|---|---|---|---|---|
| PETs (>90% esterified) | 0 | 0 | 0 | 0 | 0 | 0 | 0 | 0 | 0 |
| Cycloaliphatic epoxy resin | 0 | 0 | 0 | 0 | 0 | 0 | 0 | 0 | 0.05 |
| Talc | 0 | 0 | 0 | 0 | 0 | 0 | 0 | 0 | 0 |
| $H_3PO_4$ (45%) | 0 | 0 | 0 | 0 | 0 | 0 | 0 | 0 | 0 |
| Fumed Silica | 0 | 0 | 0 | 0 | 0 | 0 | 0 | 0 | 0 |
| Tospearl ™ 120 | 0 | 0 | 0 | 0 | 0 | 0 | 0 | 0 | 0 |
| Total | 100 | 100 | 100 | 100 | 100 | 100 | 100 | 100 | 100 |
| Wt % Si | 2.25 | 2.25 | 2.25 | 2.25 | 3.00 | 3.00 | 4.00 | 4.00 | 2.25 |

TABLE 2

Formulations and properties for Examples 10-18.

| Description | Ex 10 | Ex 11 | Ex 12 | Ex 13 | Ex 14 | Ex 15 | Ex 16 | Ex 17 | Ex 18 |
|---|---|---|---|---|---|---|---|---|---|
| PC-PS1 | 0 | 0 | 0 | 0 | 0 | 0 | 0 | 0 | 0 |
| PC-PS2 | 20 | 11.25 | 20 | 11.25 | 20 | 11.25 | 20 | 11.25 | 20 |
| PC1 | 79.54 | 83.19 | 74.44 | 85.34 | 76.59 | 86.34 | 77.59 | 88.34 | 79.54 |
| PC2 | 0 | 0 | 0 | 0 | 0 | 0 | 0 | 0 | 0 |
| Tris(di-butylphenyl) phosphite | 0.06 | 0.06 | 0.06 | 0.06 | 0.06 | 0.06 | 0.06 | 0.06 | 0.06 |
| Poly alpha olefin, 6 cS/100° C. | 0.35 | 0.35 | 0.35 | 0.35 | 0.35 | 0.35 | 0.35 | 0 | 0 |
| PETs (>90% esterified) | 0 | 0 | 0 | 0 | 0 | 0 | 0 | 0.35 | 0.35 |
| Cycloaliphatic epoxy resin | 0.05 | 0 | 0 | 0 | 0 | 0 | 0 | 0 | 0 |
| Talc | 0 | 5 | 5 | 0 | 0 | 0 | 0 | 0 | 0 |
| $H_3PO_4$ (45%) | 0 | 0.15 | 0.15 | 0 | 0 | 0 | 0 | 0 | 0 |
| Fumed Silica | 0 | 0 | 0 | 3 | 3 | 0 | 0 | 0 | 0 |
| Tospearl ™ 120 | 0 | 0 | 0 | 0 | 0 | 2 | 2 | 0 | 0 |
| Total | 100 | 100 | 100 | 100 | 100 | 100 | 100 | 100 | 100 |
| Wt % Si | 4.00 | 2.25 | 4.00 | 2.25 | 4.00 | 2.25 | 4.00 | 2.25 | 4.00 |

Examples 1-18 are formulated as prophetic examples providing certain mechanical and physical properties desirable for formation of a microneedle array. These properties include, but are not limited to: a high flow (MVR of greater than 35 cm³/min) and processing window suitable to form parts without aesthetic issues, high flow at high shear conditions (greater than $10^6$ s$^{-1}$) to allow good transcription of mold texture and excellent filling of the microneedle mold features, good strength and impact strength (as indicated by ductile Izod Notched Impact at room temperature), release properties to provide efficient de-molding and reduced cooling and cycle time during molding.

The above description is intended to be illustrative, and not restrictive. For example, the above-described examples (or one or more aspects thereof) may be used in combination with each other. Other aspects can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed aspect. Thus, the following claims are hereby incorporated into the Detailed Description as examples or aspects, with each claim standing on its own as a separate aspect, and it is contemplated that such aspects can be combined with each other in various combinations or permutations. The scope of the disclosure should be determined with reference to the appended claims, along with the full scope of equivalents to which such claims are entitled.

What is claimed:

1. A microneedle comprising a shaft having a proximal end and a distal end and a capillary space within said shaft, said capillary space (i) connecting said proximal and distal ends or (ii) extending from the distal end of the shaft and connecting with one or more external openings positioned between the proximal end and distal end or (iii) performing functions both (i) and (ii), said microneedle comprising a polymer mixture which comprises (a) optionally polycarbonate, (b) polycarbonate-polysiloxane copolymer, and (c) mold release agent.

2. The microneedle of claim 1 formed from a polymer mixture comprising:
from greater than 0 wt. % to about 94.9 wt. % polycarbonate;

about 5 wt. % to about 99.9 wt. % polycarbonate-polysiloxane copolymer; and about 0.1 wt. % to about 1 wt. % mold release agent;

wherein the combined weight percent value of all components does not exceed about 100 wt. %, and wherein all weight percent values are based on the total weight of the polymer mixture.

3. The microneedle of claim 1, wherein said polymer mixture has a melt volume flow rate (MVR) of greater than 35 cm$^3$/min as measured according to ASTM 1133 at 300° C. and 1.2 kg.

4. The microneedle of claim 1, wherein said polymer mixture has an Izod Notched Impact of at least 35 kJ/m$^2$ as measured at 3 mm thickness according to ISO 180-1A.

5. The microneedle of claim 1, wherein the polycarbonate-siloxane copolymer comprises about 4 wt. % to about 97 wt. % siloxane based on the weight of the copolymer.

6. The microneedle of claim 1, wherein said polymer mixture comprises about 70 wt. % to about 89.5 wt. % polycarbonate and about 10 to about 30 wt. % polycarbonate-siloxane copolymer.

7. The microneedle of claim 1, wherein said polycarbonate comprises interfacial polycarbonate.

8. The microneedle of claim 1, wherein said polycarbonate comprises melt polycarbonate.

9. The microneedle of claim 1, wherein said mold release agent comprises one or more of pentaerythritol stearate, glycerol monostearate, a wax, polyethylene or a poly alpha olefin.

10. The microneedle of claim 1, wherein said microneedle consists of said polymer mixture.

11. The microneedle of claim 1, wherein said polymer mixture has a heat deflection temperature (HDT) of at least 120° C. on a 3.2 mm sample at 1.8 MPa as measured according to ISO 75A.

12. A medical device suitable for delivery of a therapeutic agent, said device comprising one or more microneedles of claim 1.

13. A method of forming a microneedle comprising:
(a) placing a polymer mixture into a mold, said polymer mixture comprising (i) optionally polycarbonate, (ii) polycarbonate-polysiloxane copolymer and (iii) mold release agent, said polymer mixture being at a temperature such that it is flowable;
(b) allowing said polymer to solidify; and
(c) releasing the solidified polymer mixture from said mold.

14. The method of claim 13, wherein said polymer mixture comprises:

from greater than 0 wt. % to about 94.9 wt. % polycarbonate;

about 5 wt. % to about 99.9 wt. % polycarbonate-polysiloxane copolymer; and about 0.1 wt. % to about 1 wt. % mold release agent;

wherein the combined weight percent value of all components does not exceed about 100 wt. %, and wherein all weight percent values are based on the total weight of the polymer mixture.

15. The method of claim 13, wherein said polymer mixture has a melt volume flow rate (MVR) of greater than 35 cm$^3$/min as measured according to ASTM 1133 at 300° C. and 1.2 kg.

16. The method of claim 13, wherein the polycarbonate-siloxane copolymer comprises about 4 wt. % to about 97 wt. % siloxane.

17. The method of claim 13, wherein said polycarbonate comprises interfacial polycarbonate.

18. The method of claim 13, wherein said polycarbonate comprises melt polycarbonate.

19. The method of claim 13, wherein said mold release agent comprises one or more of pentaerythritol stearate, glycerol monostearate, polyethylene, a wax or a poly alpha olefin.

20. The method of claim 13, wherein said polymer mixture comprises about 70 wt. % to about 89.5 wt. % polycarbonate and about 10 to about 30 wt. % polycarbonate-siloxane copolymer.

\* \* \* \* \*